United States Patent
Otsubo et al.

(10) Patent No.: US 8,821,469 B2
(45) Date of Patent: Sep. 2, 2014

(54) DISPOSABLE PANTS-TYPE WEARING ARTICLE

(75) Inventors: Toshifumi Otsubo, Kanonji (JP); Tatsuya Hashimoto, Kanonji (JP); Mariko Yamashita, Kanonji (JP)

(73) Assignee: Unicharm Corporation, Ehime (JP)

( * ) Notice: Subject to any disclaimer, the term of this patent is extended or adjusted under 35 U.S.C. 154(b) by 109 days.

(21) Appl. No.: 13/521,821

(22) PCT Filed: Jan. 21, 2011

(86) PCT No.: PCT/JP2011/051124
§ 371 (c)(1),
(2), (4) Date: Jul. 12, 2012

(87) PCT Pub. No.: WO2011/090170
PCT Pub. Date: Jul. 28, 2011

(65) Prior Publication Data
US 2012/0289920 A1 Nov. 15, 2012

(30) Foreign Application Priority Data

Jan. 21, 2010 (JP) ................................. 2010-011403

(51) Int. Cl.
*A61F 13/15* (2006.01)
(52) U.S. Cl.
USPC ............ 604/385.24; 604/385.25; 604/385.27; 604/385.29; 604/385.3; 604/394; 604/396
(58) Field of Classification Search
USPC ............. 604/385.24, 385.25, 385.27, 385.29, 604/385.3, 394, 396
See application file for complete search history.

(56) References Cited

U.S. PATENT DOCUMENTS

| 4,743,241 A | 5/1988 | Igaue et al. |
| 2010/0249743 A1 | 9/2010 | Takino |

FOREIGN PATENT DOCUMENTS

| JP | 62069804 A | 3/1987 |
| JP | 62231005 A | 10/1987 |
| JP | 62243806 A | 10/1987 |
| JP | 62243807 A | 10/1987 |
| JP | 7003621 A | 1/1995 |
| JP | 7308341 A | 11/1995 |
| JP | 9313531 A | 12/1997 |
| JP | 3488506 B2 | 1/2004 |
| JP | 2008173285 A | 7/2008 |
| JP | 2009061052 A | 3/2009 |

OTHER PUBLICATIONS

International Search Report and Written Opinion for PCT/JP2011/051124, dated May 10, 2011.

*Primary Examiner* — Jacqueline F. Stephens
(74) *Attorney, Agent, or Firm* — Lowe Hauptman & Ham LLP

(57) ABSTRACT

A disposable pants-type wearing article includes belt-shaped leg elastic members. Respective opposite side edges of front and rear waist regions of the article are fusion-bonded together to define joined regions. The belt-shaped leg elastic members respectively have front side upper ends lying in the front waist region and included by the put flat and joined together regions and rear side upper ends lying in the rear waist region and included by the put flat and joined together regions. In the joined regions, lower edges of the upper ends and lower edges of the rear side upper ends are displaced one from another in such a manner that the one pair of the lower edges lies below the other pair of the lower edges.

5 Claims, 8 Drawing Sheets

FIG.1
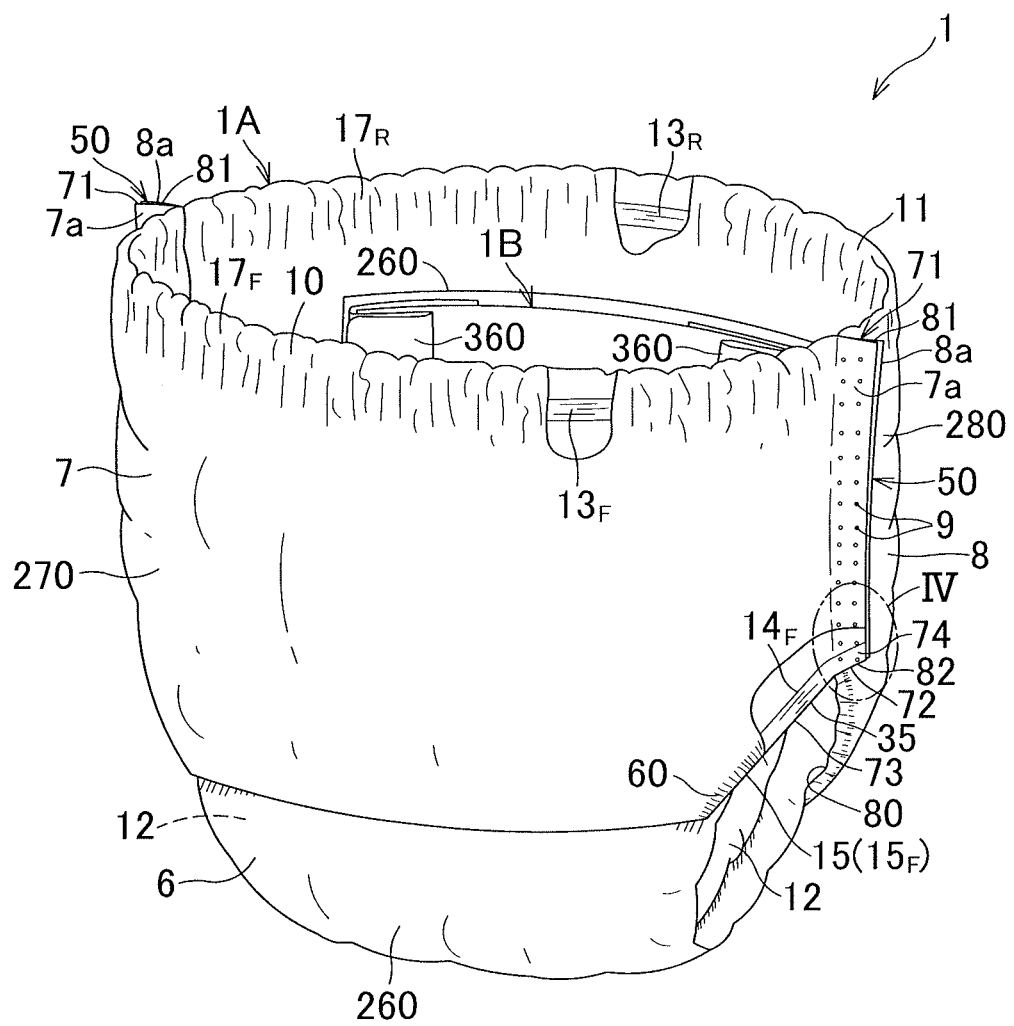
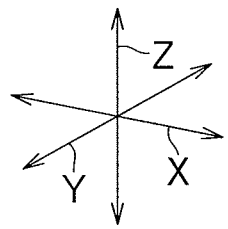

DISPOSABLE PANTS-TYPE WEARING ARTICLE

RELATED APPLICATIONS

The present application is National Phase of International Application Number PCT/JP2011/051124, filed Jan. 21, 2011, and claims priority from Japanese Application Number 2010-011403, filed Jan. 21, 2010.

TECHNICAL FIELD

The present invention relates to disposable pants-type wearing articles suitable for use as disposable diapers or the like.

BACKGROUND

Conventionally, disposable pants-type diapers which are formed by putting respective opposite side edges of front and rear waist regions flat together and bonding them together are known.

For example, in disposable absorbent pants disclosed in JP S62-243806 A (PTL 1), front and rear waist regions are put flat and joined together by sealing treatments under pressure along respective opposite side edges of these front and rear waist regions. Belt-like leg elastic members extending in a transverse direction or belt-like leg elastic members extending in a longitudinal direction are bonded to the front and rear waist regions, respectively. These leg elastic members are formed, for example, by urethane foams or the like and have a relatively large width dimension of about 10 to about 45 mm.

In the disposable diaper disclosed in JP 3488506 B2 (PTL 2), belt-like leg elastic sheet members are attached under even tension in a longitudinal direction thereof to a base material sheet forming the diaper. On the base material sheet cut in an hourglass-shape, the leg elastic sheet members respectively draw concave curved lines in a crotch region.

In the pants-type absorbent article disclosed in JP 2008-173285 A (PTL 3), a front waist region and a rear waist region are and joined together along side seal arrays by a sealing treatment such as a heat-sealing or ultrasonic sealing treatment. A plurality of straight belt-like leg-gather strips are attached to peripheral edges of respective leg-openings in a manner that these leg-gather strips may be obliquely crossed so as to draw curved lines along the peripheral edges of the respective leg-openings.

CITATION LIST

Patent Literature

{PTL 1} JP S62-243806 A
{PTL 2} JP 3488506 B2
{PTL 3} JP 2008-173285 A

SUMMARY

Technical Problem

As one example of methods to make pants-type wearing articles such as disposable pants-type diapers, the opposite side edges of the front waist region and the opposite side edges of the rear waist region may be put flat together and thermoplastic synthetic resin contained by these side edges in the form of fiber or film may be fusion-bonded under pressure by an ultrasonic sealer or the like to form put flat and joined together regions. However, the inventors found that, if belt-like elastic members made of natural or synthetic rubber are included by those side edges, these elastic members may make it difficult to fusion bond those side edges at least in regions of these side edges occupied by the elastic members. In consequence, there is possibility that the respective side edges of the front and rear waist regions certainly having been fusion-bonded together might be broken during use of the wearing article. If fibrous nonwoven fabrics or plastic films forming the respective side edges of the front and rear waist regions contain thermoplastic synthetic resins when it is desired to fusion-bond the respective side edges of the front and rear waist regions using the ultrasonic sealer, it will be easy to join the respective side edges of the front and rear waist regions so that these side edges once having been joined can not be readily broken. However, in a region wherein the belt-like leg elastic members included in the front waist region overlap the belt-like leg elastic members, respectively, it is not easy to join the respective side edges of the front and rear waist regions together so that these side edges once having been joined can not be readily broken. The problem is serious particularly when the respective belt-like leg elastic members overlap with each other in the put flat and joined together regions in the vicinity of the peripheral edges of the respective leg-opening. Specifically, vigorous movement of the wearer's legs may cause the front and rear waist regions to be separated from each other along the put flat and joined together regions.

An object of the present invention to provide the disposable pants-type wearing article improved so that, even when the belt-like leg elastic members are provided along the peripheral edges of the leg-openings, the front and rear waist regions are not readily separated from each other along the put flat and joined together regions defined by the respective opposite side edges of the front and rear waist regions.

Solution to Problem

Some embodiments of the present invention provide a disposable pants-type wearing article described as follows.

A disposable pants-type wearing article having a front-back direction, a vertical direction and a transverse direction being orthogonal to one another; the article including:

a front waist region and a rear waist region opposed to each other in the front-back direction and a crotch region extending between these two waist regions;

put flat and joined together regions formed by putting flat and joining together the front and rear waist regions along respective side edges of the front and rear waist regions respectively opposed in the transverse direction and extending in the vertical direction;

a waist-opening and a pair of leg-openings formed by cooperation of the front and rear waist regions with the crotch region;

belt-like leg elastic members extending under tension along respective peripheral edges of the leg-openings; and the belt-like leg elastic members respectively contain at least one of natural rubber and synthetic rubber so as to be provided with stretch property and have a skin-facing side of the wearing article covered with a sheet-like member formed of at least one of a nonwoven fabric and a plastic film.

The belt-like leg elastic members respectively include, in addition, front side upper ends lying in the front waist region and rear side upper ends lying in the rear waist region both included by the put flat and joined together regions wherein the front side upper ends and the rear side upper ends respectively include, in the put flat and joined together regions, lower edges of the belt-like leg elastic members and the other lower edges extending in parallel to the lower edges; and the lower edges of the front side upper ends and the other lower edges of the rear side upper ends in the put flat and joined together regions are displaced from each other in the vertical direction so that the one pair of the lower edges lie below the other pair of the lower edges wherein the one pair of the lower edges are fusion-bonded to the sheet-like member covering the other pair of the lower edges at a level lower than the other pair of the lower edges.

According to one embodiment of the present invention, a pair of the lower edges and edges being contiguous thereto and extending circumferentially about the wearer's legs respectively define parts of entire peripheral edges of the leg-openings.

According to another embodiment of the present invention, the one pair of the lower edges and edges being contiguous thereto and extending circumferentially about the wearer's legs respectively cause, upon contraction of the belt-like leg elastic members, the sheet-like member to be formed along the parts of entire peripheral edges of the leg-openings with frills.

According to still another embodiment of the present invention, the one pair of the lower edges are included by the front side upper ends and the other pair of the lower edges are included by the rear side upper ends.

As used herein, the term "belt-like leg elastic members" means the elastic members each having the dimension in the transverse direction at least 1.5 times the dimension in the thickness direction.

As used herein, the description "the sheet-like member is formed with frills" means that, upon contraction of the belt-like leg elastic members attached under tension to the sheet-like member, the edge of the sheet-like member spaced from the belt-like leg elastic members and extending in parallel to these belt-like leg elastic members is deformed so as to be undulated. The undulation is repeated in the direction in which the belt-like leg elastic members contract.

Advantageous Effects of Invention

In the disposable pants-type wearing article according to the present invention, the lower edges included by the front side upper ends of the belt-like leg elastic members and the other lower edges included by the rear side upper ends are displaced from each other in the vertical direction in the put flat and joined together regions so that the one pair of the lower edges lie below the other pair of the lower edges. The one pair of the lower edges are fusion-bonded to the sheet-like member covering the other pair of the lower edges at a level lower than the other pair of the lower edges. With such arrangement, there is no possibility that the belt-like leg elastic members for the respective leg-openings might overlap each other and be bonded together along the peripheral edges of the respective leg-openings. In consequence, the side edges of the front and rear waist regions put flat and joined together should readily begin to be peeled off one from another from the peripheral edges of the respective leg-openings.

BRIEF DESCRIPTION OF DRAWINGS

FIG. 1 is a partially cutaway perspective view of a disposable pants-type wearing article (pants-type diaper).

DESCRIPTION OF EMBODIMENTS

Details of a disposable pants-type wearing article according to the present invention will be more fully understood from the description given hereunder with reference to the accompanying drawings.

Figure 2:
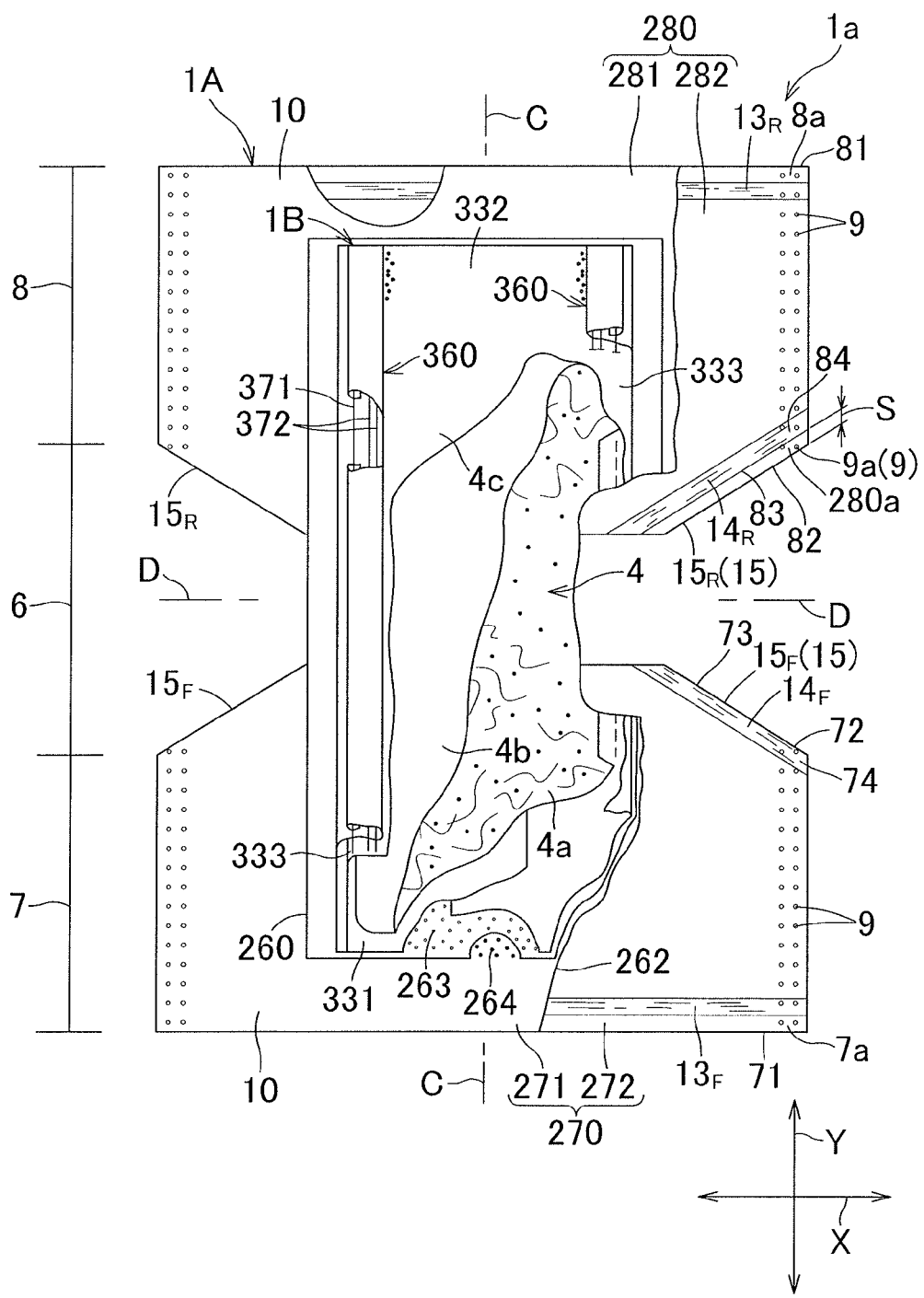
FIG. 2 is a partially cutaway plan view of the flatly developed diaper.

FIG. 1 a partially cutaway perspective view of a pants-type diaper 1 as one example of the disposable pants-type wearing articles according to the present invention wherein a transverse direction, a front-back direction and a vertical direction are denoted by double-headed arrows X, Y and Z, respectively. The diaper 1 includes a pants-shaped chassis 1A and a bodily fluid-absorbent structure 1B attached to an inner surface of the chassis 1A. The chassis 1A includes a crotch region 6, a front waist region 7 extending forward with respect to the crotch region 6 and a rear waist region 8 extending rearward with respect to the crotch region 6. The front and rear waist regions 7, 8 are put flat and joined together along respective opposite edges 7a 8a thereof by sealing spots 9 arranged intermittently in the vertical direction Z to form put flat and joined together regions 50. In the diaper 1, the front and rear waist regions 7, 8 cooperate with the crotch region 6 to form a waist-opening 11 and a pair of leg-openings 12. The chassis 1A further includes a front sheet assembly 270 extending over a whole area of the front waist region 7 and additionally over an upper half of the crotch region 6 on its front side and a rear sheet assembly 280 extending over a whole area of the rear waist region 8 and additionally over a upper half of the crotch region 6 on its rear side (See FIGS. 2 and 3). The front sheet assembly 270 is provided with a belt-like front waist-elastic member $13_F$ extending along a peripheral edge 10 of the waist-opening 11 and belt-like front side leg elastic members $14_F$ extending along front halves $15_F$ of the peripheral edges 15 of the respective leg-openings 12 are attached under tension to the front sheet assembly 270. The rear sheet assembly 280 is provided with a belt-like rear waist-elastic member $13_R$ extending along a peripheral edge 10 of the waist-opening 11 and belt-like rear side leg elastic members $14_R$ extending along rear side peripheral edges $15_R$ of the respective leg-openings 12 as shown in FIG. 2 are attached under tension to the front sheet assembly 270. It should be appreciated that these elastic or elastic members, $13_F$, $13_R$, $14_F$ and $14_R$ are in a contracted state in the diaper 1 shown in FIG. 1.

Figure 3:
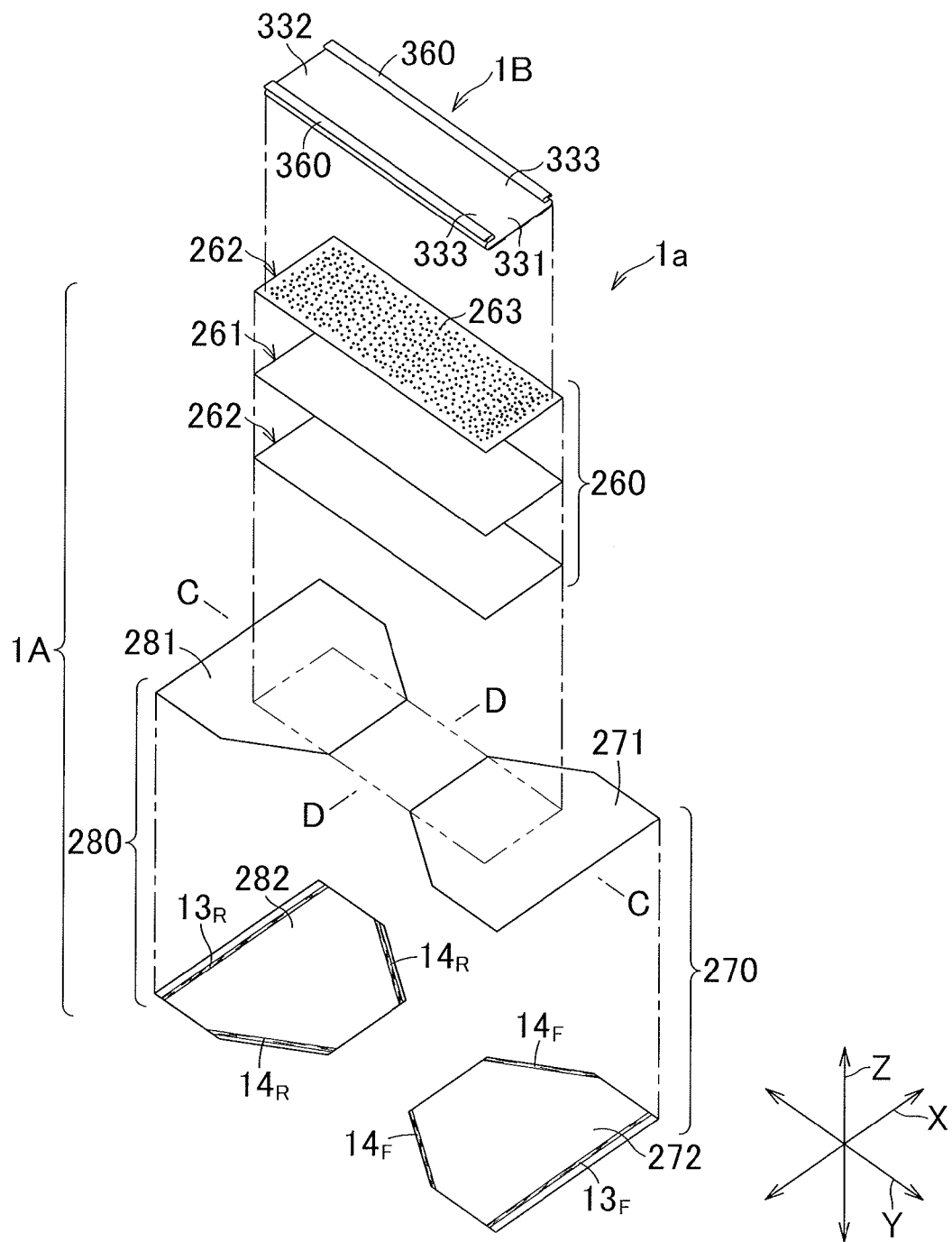
FIG. 3 is an exploded perspective view of the flatly developed diaper.

FIG. 2 is a partially cutaway plan view of the diaper $1a$ having the front and rear waist regions 7, 8 peeled off from each other along the put flat and joined together regions 50 and flatly developed in the transverse direction X and the front-back direction Y, and FIG. 3 is an exploded perspective view of the flatly developed diaper $1a$. The respective regions extending in the vertical direction Z in FIG. 1 extend in the front-back direction Y in FIGS. 2 and 3. In FIG. 2, a front-back center line C-C and a transverse center line D-D extending orthogonally to the front-back center line C-C to bisect a dimension of the developed diaper $1a$ in the front-back direction Y are indicated. The developed diaper $1a$ is shaped symmetrically about the front-back center line C-C.

Referring to FIGS. 2 and 3, the chassis 1A includes a substantially hexagonal front sheet assembly 270 defining the front waist region 7, a substantially hexagonal rear sheet assembly 280 defining the rear waist region 8 and part of the crotch region 6 and a rectangular central sheet assembly 260 defining part of the crotch region 6.

The front sheet assembly 270 includes an inner sheet 271 and an outer sheet 272 which are the same in shape as well as in size. Between these sheets 271, 272, the single belt-like front waist-elastic member $13_F$ and a pair of front side leg-elastic members $14_F$ are sandwiched and attached under tension to at least one of these inner and outer sheets 271, 272 with hot melt adhesives (not shown). The respective inner surfaces of the elastic or elastic members $13_F$, $14_F$ facing the wearer's skin (not shown) is covered with the inner sheet 271.

The rear sheet assembly 280 includes an inner sheet 281 and an outer sheet 282 which are the same in shape as well as in size. Between these sheets 281, 282, the single belt-like rear waist-elastic member $13_R$ and a pair of front side leg-elastic members $14_R$ are sandwiched and attached under tension to at least one of these inner sheet 281 and outer sheet 282 with hot melt adhesives (not shown). The respective inner surfaces of the elastic members $13_R$, $14_R$ facing the wearer's skin (not shown) is covered with the inner sheet 281.

The central sheet 260 includes a rectangular leakage-barrier plastic film 261 sandwiched between a pair of cover sheets 262 wherein these film and sheets are bonded one to another with hot melt adhesives (not shown). The preferred leakage-barrier plastic film 261 is formed of moisture-permeable but liquid-impervious plastic film and the preferred cover sheet 262 is formed of a fibrous nonwoven fabric. Front and rear ends of the central sheet assembly 260 respectively extend onto respective inner surfaces (i.e., upper surfaces as viewed in FIG. 3) of the front sheet assembly 270 and the rear sheet assembly 280 and are respectively bonded to these inner surfaces with hot melt adhesives 264 (See FIG. 2) so as to connect the front sheet assembly 270 with the rear sheet assembly 280. The bodily fluid-absorbent structure 1B is bonded to the inner surface of the central sheet assembly 260 with hot melt adhesives 263 applied to the inner surface of the central sheet assembly 260.

Referring to FIG. 2, the bodily fluid-absorbent structure 1B has a rectangular shape which is relatively long in the front-back direction and this shape is contoured by a pair of opposite side edges 333 extending in parallel to the center line C-C and front and rear ends 331, 332 extending in parallel to the center line D-D. The respective side edges 333 are formed with leakage-barriers 360 of in the name of the three dimensional gather in the art. In such bodily fluid-absorbent structure 1B, an assembly of bodily fluid absorbent material $4a$ such as fluff pulp and super-absorbent polymer particles is covered with a wrapping sheet $4b$ formed of a liquid-previous tissue paper or a fibrous nonwoven fabric and the side of this wrapping sheet $4b$ facing the wearer's skin is covered with a liquid-previous skin-contact sheet $4c$. The leakage-barriers 360 are preferably formed of a liquid-impervious sheet. High leakage-barrier effect of the bodily fluid-absorbent structure 1B is assured by the leakage-barriers 360 and indirect back up of the liquid-impervious inner sheet 261 constituting the central sheet assembly 260.

Rubber threads 371, 372 extending in the front-back direction Y as viewed in FIG. 2 are bonded under tension to the liquid-impervious sheet forming the leakage-barriers 360 of the bodily fluid-absorbent structure 1B with means of hot melt adhesives (not shown). While the liquid-impervious sheet is folded in a Z-shape or in an inverted Z-shape in the developed diaper $1a$ of FIG. 2, the leakage-barriers 360 raise themselves on the inner surface of the skin-contact sheet $4c$ along the side edges 333 of the bodily fluid-absorbent structure 1B under contraction of the rubber threads 371, 372.

In the diaper 1 as has been described above, the inner sheets 271, 281 and the outer sheets 272, 282 may be formed of sheet-like members such as fibrous nonwoven fabrics containing thermoplastic synthetic fibers, plastic films formed from thermoplastic synthetic resins or a laminated of these nonwoven fabric and plastic film. More preferably, these inner and outer sheets 271, 281; 272, 282 may be formed of spun bonded nonwoven fabrics, melt blown nonwoven fabrics or SMS nonwoven fabrics as a laminate of spun bonded nonwoven fabrics, melt blown nonwoven fabrics and spun bonded nonwoven fabrics. In every case, a mass per unit area thereof is about 10 to about 100 $g/m^2$. The front side belt-like leg elastic members $14_F$ and the rear side belt-like leg elastic members $14_R$ may be formed of belt-like sheets containing at least one of natural rubber and synthetic rubber as rubber ingredients. These belt-like leg elastic members $14_F$, $14_R$ may be preferably formed of elastically stretchable fibrous nonwoven fabrics made of elastic yarns or threads containing urethane rubber or the like as rubbers ingredients or plastic films having a mass per unit area ranging from about 20 to 100 $g/m^2$. More preferably, these belt-like leg elastic members $14_F$, $14_R$ may be formed of the elasticized fibrous nonwoven fabrics made of elastic yarns or threads containing the rubber ingredients such as urethane rubbers or the elasticized fibrous nonwoven fabrics including elastic yarns or threads and inelastic thermoplastic synthetic fibers wherein the elastic yarns or threads of at least about 30% by mass are contained therein. Referring to FIG. 2, both a width dimension $W_F$ of the front side leg elastic member $14_F$ and a width dimension $W_R$ of the rear side leg elastic member $14_R$ are the dimensions measured in the direction which is orthogonal to the direction in which these elastic members extend. These width dimensions $W_F$ and $W_R$ are preferably at least about 5 mm and more preferably ranging from about 7 to about 40 mm. Thickness dimension of these elastic members $14_F$, $14_R$ is preferably about 0.2 to about 1.5 mm. Thickness dimensions of the fibrous nonwoven fabrics, the plastic films, the belt-like waist-elastic members $13_F$, $13_R$ and the belt-like leg elastic members $14_F$, $14_R$ as have been indicated were values measured using Automatic Compression Tester "KES-FB3-AUTO-A" (manufactured by KATO TECH CO., LTD. in Japan) when compression force of about 0.5 $g/cm^2$ was exerted on the respective test pieces.

While the front waist-elastic member $13_F$ and the rear waist-elastic member $13_R$ in the developed diaper $1a$ are preferably belt-like elastic members each having a width dimension ranging from about 10 to about 40 mm, it is also possible to use a plurality of rubber threads each having a diameter or a width dimension ranging from about 0.3 to about 3 mm as the front waist-elastic member $13_F$ and the rear waist-elastic member $13_R$. In the developed diaper $1a$, the front waist-elastic member $13_F$ and the front side leg elastic members $14_F$ are in a state appropriately stretched in the longitudinal direction, for example, at a ratio of about 1.5 to about 4.0 and the rear waist-elastic member $13_R$ and the rear side leg members $14_R$ are also in a state appropriately stretched in the longitudinal direction, for example, at a ratio of about 1.5 to about 4.0.

Figure 4:
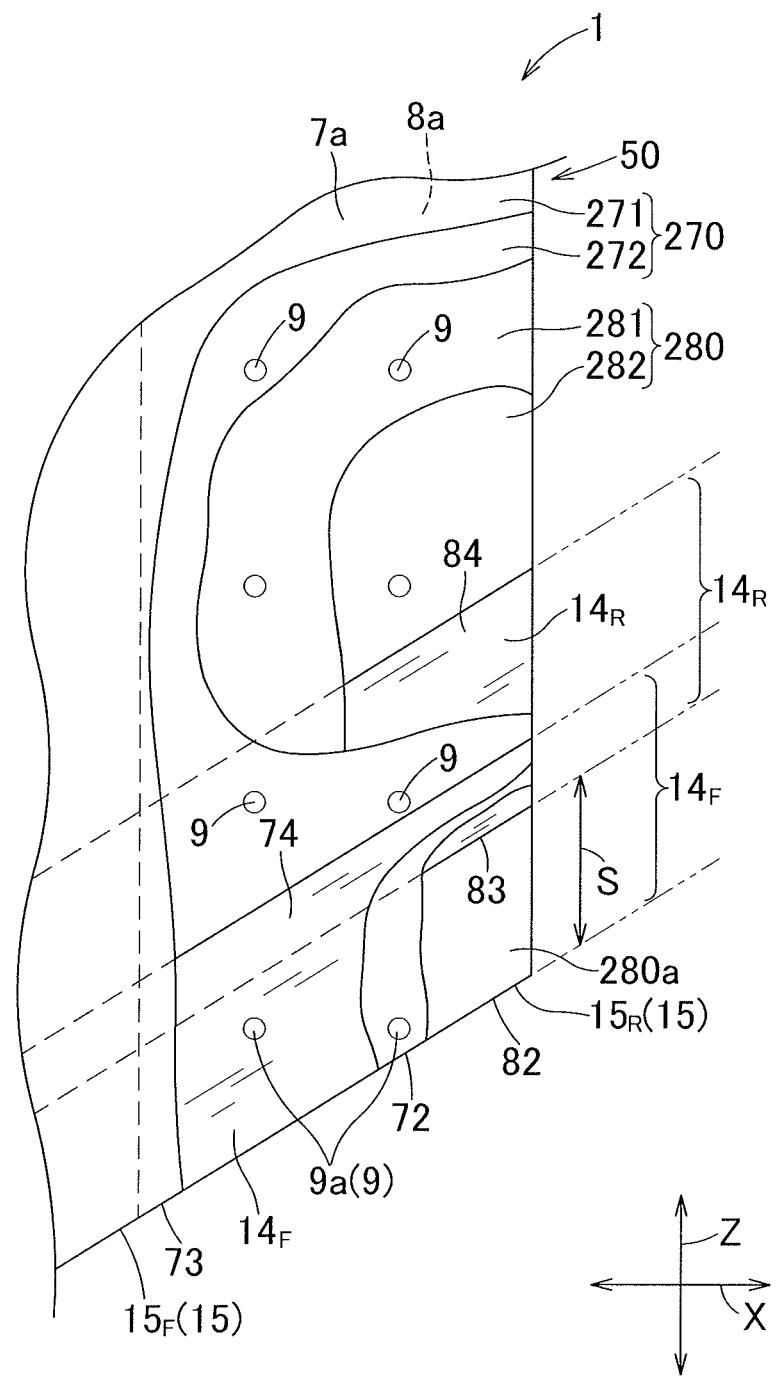
FIG. 4 is a partially cutaway plan view of a region IV in FIG. 1.

FIG. 4 is a partially cutaway plan view of a region enclosed by an imaginary line IV in FIG. 1. The developed diaper $1a$ of FIG. 2 is folded back along the center line D-D with the bodily fluid-absorbent structure 1B inside and thereby the respective side edges 7a; 8a of the front and rear waist regions 7, 8 are put flat together. The side edges 7a; 8a put flat together in this manner may be set between horns and anvils of an ultrasonic sealer and ultrasonic treated to form a plurality of sealing spots 9 in which the respective side edges 7a; 8a of the front and rear waist regions 7, 8 are joined and these sealing spots 9 form the respective put flat and joined together regions 50. Now the developed diaper 1a is converted to the flat diaper 1 under tension in the transverse direction X as well as in the longitudinal direction Y. In the developed diaper 1a, a dimension of the side edge 7a in the front-back direction Y is same as that of the side edge 8a in the front-back direction Y and upper and lower edges 71, 72 of the side edge 7a in the put flat and joined together regions 50 (See FIG. 1) of the diaper 1 coincide with upper and lower ends 81, 82 of the side edge 8a, respectively.

As will be apparent from FIG. 4 in combination with FIGS. 1 and 2, the front side leg elastic elements $14_F$ respectively include lower edges 73 extending in accordance with the front side peripheral edges $15_F$ of the respective leg-openings 12 and front upper ends 74 overlapping the side edges 7a of the front waist region 7 and included in the put flat and joined together regions 50. The rear side leg elastic elements $14_R$ respectively include lower edges 83 extending in parallel to the rear side peripheral edges $15_R$ at a distance S from the rear side peripheral edges $15_R$ and rear side upper ends 84 overlapping the side edges 8a of the rear waist region 8 and included in the put flat and joined together regions 50. Of the rear side peripheral edges $15_R$, segments 280a defined between the lower edges 83 of the rear side leg elastic members $14_R$ and the rear side peripheral edges $15_R$ each spaced from the associated lower edge 83 by a distance S are respectively formed of the inner sheet 281 and the outer sheet 282 and include none of the rear side leg elastic members $14_R$. It should be noted here that the distance S indicates a dimension measured in parallel to the center line C-C.

In the put flat and joined together regions 50 each including the front side upper end 74 and the rear side upper end 84 as have been described just above, the side edges 7a; 8a are fusion-bonding treated under pressure by an ultrasonic sealer or the like and thereby thermoplastic synthetic resins contained in the side edges 7a; 8a are fusion-bonded together. During this treatment, the front side upper ends 74 and/or the inner sheet 271 covering these front side upper ends 74 may be fusion-bonded to at least one of the inner sheet 281 and the outer sheet 282 in the side edges 8a, more preferably to both the inner sheet 281 and the outer sheet 282 to form the sealing spots 9 including none of the rear side leg elastic members 14R and thereby to join the side edges 7a to the side edges 8a. When the side edges 7a are joined to the side edges 8a, in regions wherein the front side leg elastic members $14_F$ overlap the rear side leg elastic members $14_R$, the presence of ingredients having rubber elasticity contained in the front side leg members $14_F$ and the rear side leg members $14_R$ would otherwise make it difficult to join the side edges 7a to the side edges 8a so surely that these side edges once having been joined together might be unintentionally peeled off one another. However, in the diaper 1 according to the present invention, even if the front side upper ends 74 of the front side leg elastic members $14_F$ are included in the lower edges 72 of the side edges 7a, the thermoplastic synthetic resins contained in the front side upper end 74 and the inner sheet 281 covering this front side upper end 74 may be fusion-bonded to the thermoplastic synthetic resins contained in the inner sheet 281 and the outer sheet 282 in the segments 280a in the side edges 8a under pressure. In this way, the side edges 7a can be firmly joined to the side edges 8a in the vicinity of the peripheral edges 16 of the respective leg-openings 12. The segments 280a of the inner sheet 281 an the outer sheet 282 used in this manner may have a dimension S sufficient to form several sealing spots 9, specifically, each of the segments 280a preferably has at least about 3 mm and more preferably has at least about 5 mm. If the value of the dimension S is at least about 5 mm, portions of the rear sheet assembly 280 which are contiguous to the segments 280a and extend along the respective rear side peripheral edges $15_R$ can be easily formed with frills 80 (See FIG. 1) adapted to be visually recognized from behind the diaper 1. However, in the front sheet assembly 270, the front side leg elastic members $14_F$ define the front side peripheral edges $15_F$. In consequence, small wrinkles 60 may be formed but the frills 80 is formed in the front sheet assembly 270. Depending on the dimension S, it is possible to design the diaper 1 in the manner that the front side peripheral edges $15_F$ of the complete peripheral edges 15 of the respective leg-openings 12 have no frills 80 but the rear side peripheral edges are formed with the frills 80. It is also possible by reducing the value of the dimension S to design the diaper 1 in the manner that not only the front side peripheral edges $15_F$ but also the rear side peripheral edges $15_R$ are not formed with the frills 80. It should be noted here that the planar shape of the individual sealing spots 9 is not specified but an appropriate planar shape may be selected from various shapes such as a dot geometry, a rectilinear shape and a curved line shape and the sealing spots may be appropriately distributed in the put flat and joined together regions 50. In the dot geometry, an area of the individual sealing spot preferably ranges from about 2 to about 5 $mm^2$.

Figure 5:
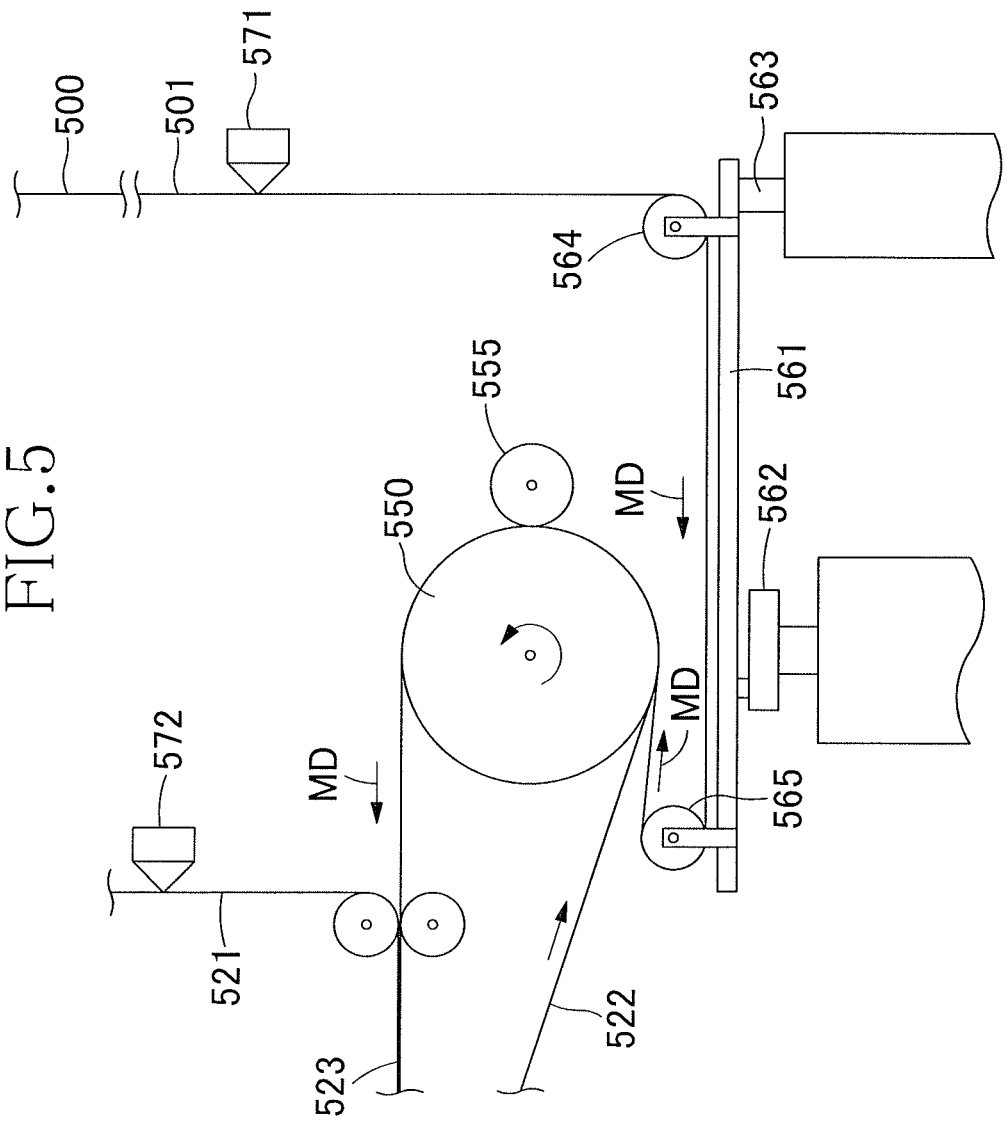
FIG. 5 is a schematic side view of a main equipment used in a process for making a composite web.
Figure 6:
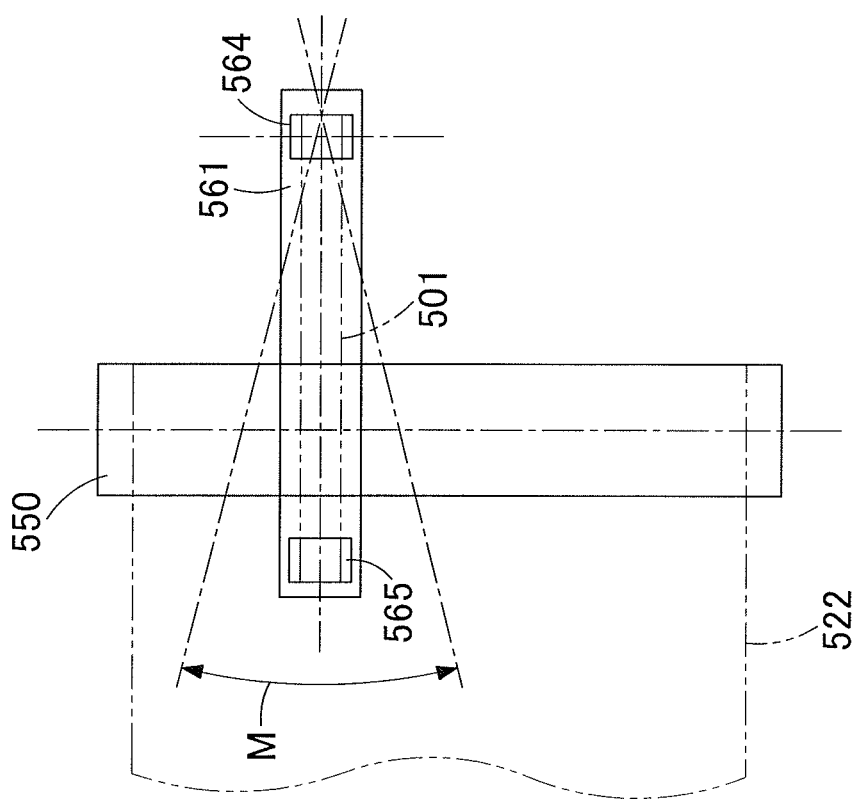
FIG. 6 is a schematic overhead view illustrating a part of FIG. 5.

FIG. 5 is a schematic side view of main equipment used in a process for making the front sheet assembly 270 and the rear sheet assembly 280 exemplarily shown in FIGS. 2 and 3 and FIG. 6 is a schematic overhead view illustrating part of the main equipment. The method for making the sheet assembly is basically common to the front sheet assembly 270 and the rear sheet assembly 280 and, in view of this, description of the method will be made hereunder with respect to the front sheet assembly 270. Referring to FIG. 5, an elastic web 501 as material webs for the front side leg elastic member $14_F$ is continuously fed from above as viewed in FIG. 5 and coated by a first coater 571 with hot melt adhesives (not shown). The elastic web 501 corresponds to a raw fabric 500 having stretch properties and having been elastically stretched at a desired ratio. The elastic web 501 is guided by guide rolls 564, 565 mounted on a rocking arm 561 and fed in a machine direction MD indicated by an arrow to a joining roll 550 on which the elastic web 501 comes in contact with and bonded under a pressure to second nonwoven fabric web 522 continuously fed from the left-hand as viewed in FIG. 5. The second nonwoven fabric web 522 further runs in the direction indicated by an arrow and converges with first nonwoven fabric web 521 which is, in turn, fed from above as viewed in FIG. 5 and coated by a second coater 572 with hot melt adhesives (not shown). In this way, the second nonwoven fabric web 522 is bonded to the first nonwoven fabric web 521 to form a composite web 523 sandwiching the elastic web 501 between these first nonwoven fabric web 521 and the second nonwoven fabric web 522. The first nonwoven fabric web 521 in the composite web 523 is used as one of the inner sheet 271 and the outer sheet 272 and the second nonwoven fabric web 522 in the composite web 523 is used as the other of the inner sheet 271 and the outer sheet 272. The rocking arm 561 is rocked to and from around a pivot shaft 563 by a driving unit 562 in a predetermined range of movement indicated by a double-headed arrow M in FIG. 6. In FIG. 6, the elastic web 501 and the second nonwoven fabric web 522 are indicated by imaginary lines.

Figure 7:
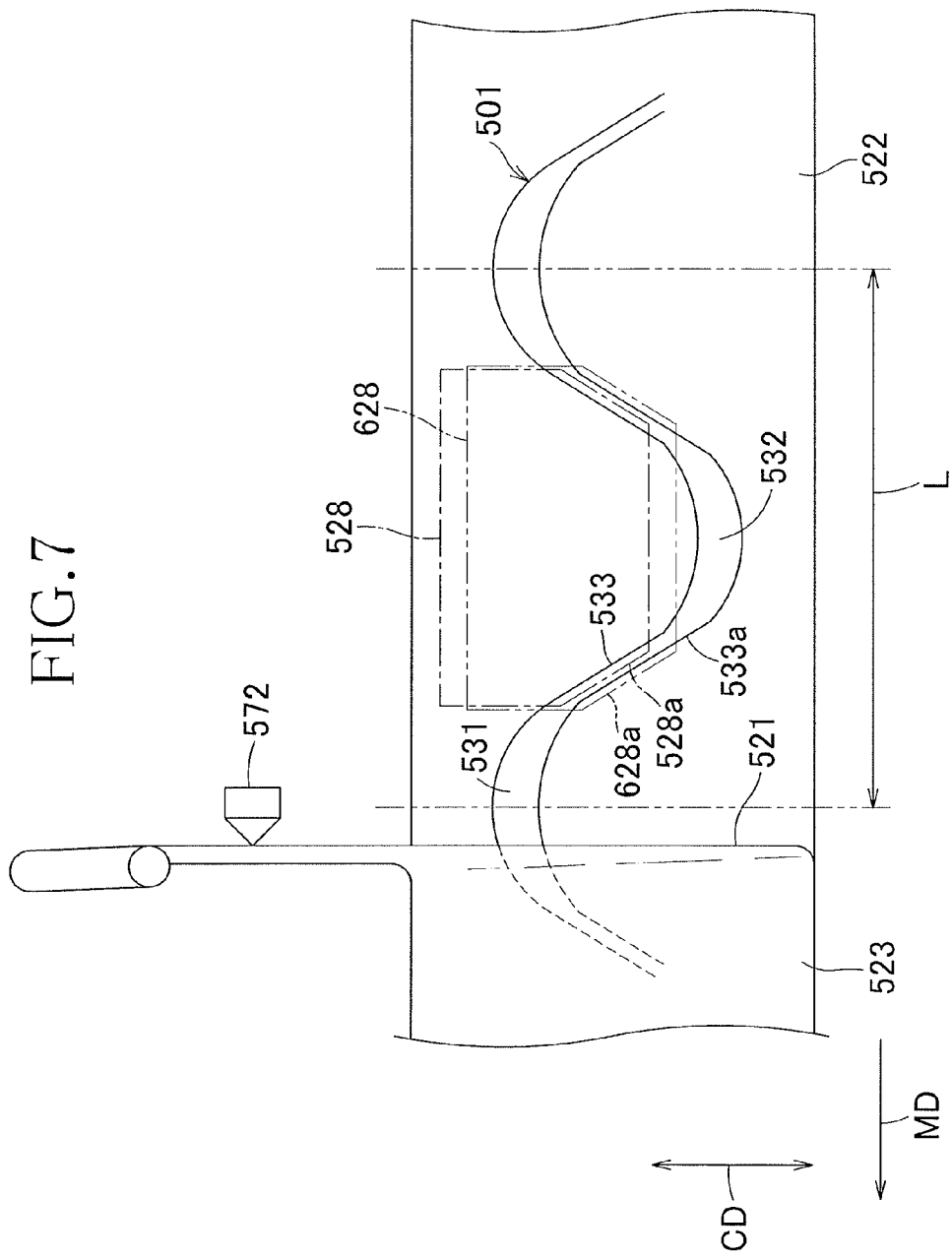
FIG. 7 is a diagram illustrating a pattern in which the composite web is bonded to a fibrous nonwoven fabric web.

FIG. 7 is a partial plan view of the second nonwoven fabric web 522 to which the elastic web 501 has been bonded. On the left-hand in FIG. 7, the first nonwoven fabric web 521 and the composite web 523 also are shown. An imaginary line 528 on the second nonwoven fabric web 522 indicates a line along which the front sheet assembly 270 is to be cut off from the composite web 523 (See FIG. 5). While illustration of the front side waist-elastic member $13_F$ to be attached to the front sheet assembly 270 is eliminated from the composite web 523 in FIG. 7, the front side leg members $13_F$ or the elastic web (not shown) formed by such members $13_F$ continuously arranged in the machine direction MD may have been attached under tension in the machine direction MD to the first nonwoven fabric web 522.

According to one embodiment of the method using the steps as illustrated in FIGS. 5 and 6 to obtain the composite web 523 shown by FIG. 7, the second nonwoven fabric web 522 corresponds to the outer sheet 272 in the diaper 1. As this second nonwoven fabric web 522, spun bonded nonwoven fabric made of polypropylene fibers and having a mass per unit area of about 25 g/m$^2$ is used and fed in the machine direction MD at a rate of about 70 m/min. As the raw fabric 500 for the elastic web 501, spun bonded nonwoven fabrics including, for example, polyurethane fibers of about 47% by mass and polypropylene fibers of about 53% by mass is used. The spun bonded nonwoven fabrics have a mass per unit area of about 30 g/m$^2$ and a width dimension of 80 mm. Such raw fabric 500 is elastically stretched at a ratio of about 3.0 in the machine direction MD and fed in the form of the elastic web 501 to the guide roll 564 as illustrated in FIG. 5. This elastic web 501 has been coated with hot melt adhesives about at a rate of about 3 g/m$^2$. The rocking arm 561 has its amplitude set to 166 mm and is rocked in such a mode that the second nonwoven fabric web 522 runs by a length L of about 340 mm in the machine direction MD for each cycle of the rocking arm's movement. The elastic web 501 guided by the rocking arm 561 is fed, in a generally sine-wave pattern, onto the second nonwoven fabric web 522. Under the rocking operation of the arm 561, the elastic web 501 has its width dimension enlarged along crest segments 531 and the trough segments 532. Along intermediate segments 533 each defined between a pair of the adjacent crest segment 531 and the trough segment 532, a plurality of gathers (not shown) undulating in the transverse direction and the width dimension of the elastic web 501 us correspondingly reduced as illustrated. Depending on the operating condition of the equipment of FIGS. 5 and 6 as well as the stretch property of the raw fabric 500, the elastic web 501 obtained by stretching the raw fabric 500 having a width dimension of 80 mm before it is stretched has its stretch ratio and width dimension varied in the course of being fed onto the second nonwoven fabric web 522 via the rocking arm 561. Specifically, the stretch ratio along the crest segment 531 and the trough segment 532 of the curve becomes lower than the stretch ratio along the intermediate segment 533. More specifically, the width dimension of the raw fabric 500 is reduced to about 32 mm along the crest segment 531 and the trough segment 532 and to about 21 mm at the narrowest portion along the intermediate segment 533. While the elastic web 501 is formed along the intermediate segment 533 with a plurality of gathers (not shown) extending in the length direction, the crest segment 531 and the trough segment 532 are substantially free from such gathers. The first nonwoven fabric web 521 lapped on the second nonwoven fabric web 522 corresponds to the inner sheet 271 in the diaper 1. Spun bonded/melt blown/spun bonded nonwoven fabrics (SMS nonwoven fabrics) made of polypropylene fibers having a mass per unit area of about 15 g/m$^2$ and width dimension of about 200 mm used as this first nonwoven fabric web 521 has been coated with hot melt adhesives at a rate of about 3 g/m$^2$. The composite web 523 formed of these first and second nonwoven fabric webs 521, 522 and the elastic web 500 is cut out in a shape as illustrated by the imaginary line 528 and used as the front sheet assembly 270 of FIG. 2. The intermediate segments 533 of the elastic web 501 are laid on the front sheet assembly to form the belt-like front leg elastic members $14_F$.

An imaginary line 628 in FIG. 7 is a predetermined line along which the rear sheet assembly 280 (See FIGS. 2 and 3) will be cut out from the composite web 523. The imaginary line 628 is coincident with the imaginary line 528 in the machine direction MID but displaced downward from the imaginary line 528 in the cross direction CD. Specifically, regions 628a of the imaginary line 628 predetermined to define the rear side peripheral edges $15_R$ of the leg-openings 12 lie below lower edges of the intermediate segments 533 of the elastic web 501. The rear sheet assembly 280 may be cut out in accordance with the imaginary line 628 to obtain the segments 280a of the rear side peripheral edges $15_R$ defined between the lower edges 83 of the rear side leg elastic members $14_R$ and the rear side peripheral edges $15_R$ each spaced from the associated lower edge 83 by the distance S as will be apparent from FIGS. 2 and 3. When the first nonwoven fabric web 521 and the second nonwoven fabric web 522 are used to form the rear sheet assembly 280, the first nonwoven fabric web 521 may be used as one of the inner and outer sheets 281, 282 and the second nonwoven fabric web 522 may be used as the other of the inner and outer sheets 281, 282. While the rear sheet assembly 280 obtained by the method as illustrated by FIG. 7 is the same as the front sheet assembly 270 so far as the shape and the component webs are concerned, it is possible to implement the present invention so that the front sheet assembly 270 and the rear sheet assembly 280 are different from each other in view of the shape or the component webs.

Figure 8:
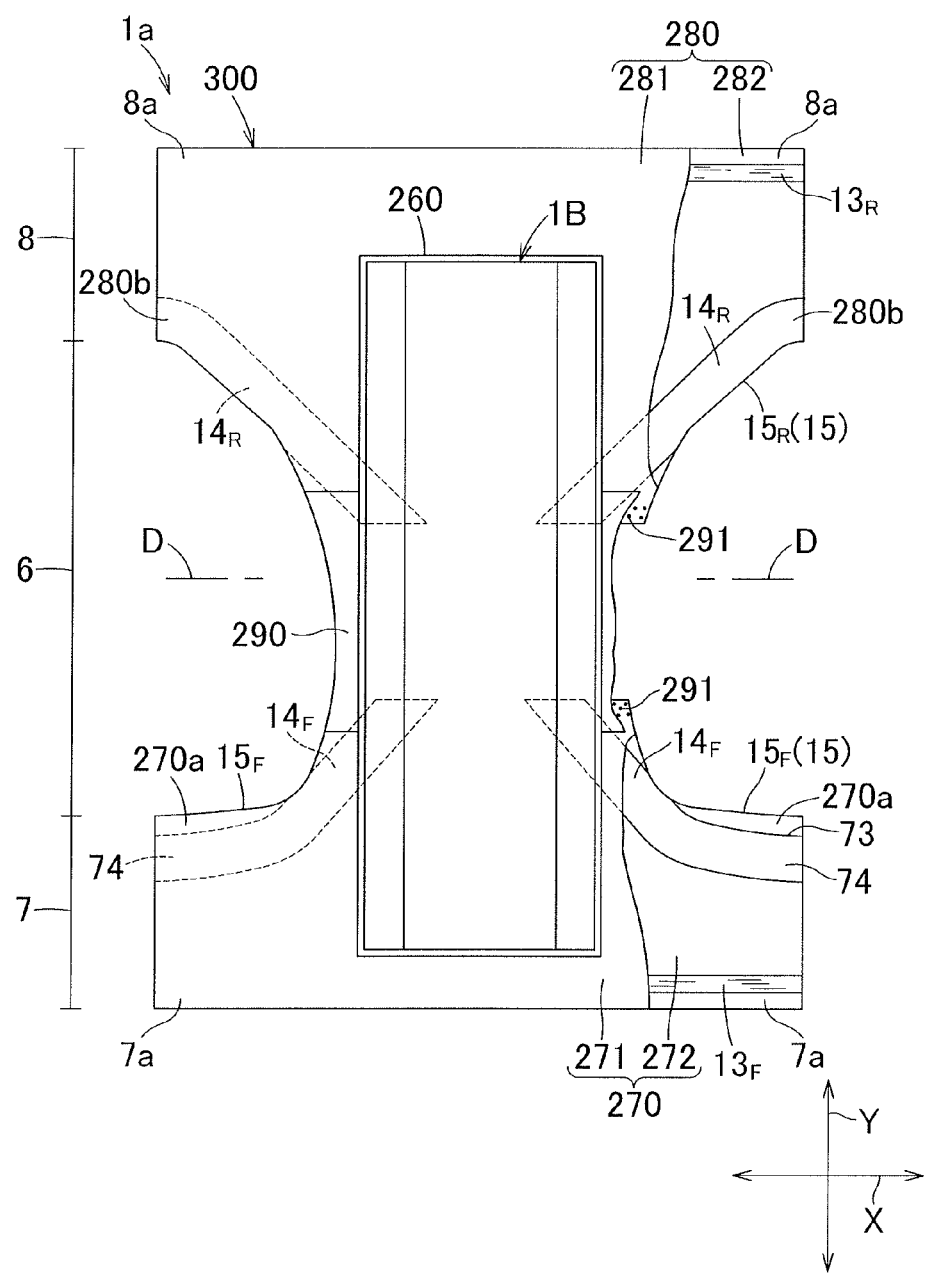
FIG. 8 is a view similar to FIG. 2, exemplarily showing one embodiment of the present invention.

FIG. 8 is a partially cutaway plan view similar to FIG. 2, showing another embodiment of the present invention. From the developed diaper 1a shown in FIG. 8 also, it is possible to obtain a diaper (not shown) having the same outer shape as the diaper 1 of FIG. 1. In the developed diaper 1a shown in FIG. 8, the regions similar to those shown in FIGS. 1 and 2 are designated by the reference numerals similar to those in FIGS. 1 and 2. It should be noted here that respective planar shapes of the front sheet assembly 270, the rear sheet assembly 280, the front side leg elastic members $14_F$ and the rear side leg elastic members $14_R$ are different from those in FIG. 2. It should be also noted that the general shapes of the belt-like front side leg elastic members $14_F$ and the belt-like rear side leg elastic members $14_R$ are indicated by solid lines and chain lines in FIG. 8. In the developed diaper 1a of FIG. 8, the front sheet assembly 270 and the rear sheet assembly 280 are bonded to a sheet strip 290 of nonwoven fabric with hot melt adhesives 291 to form an hourglass-shaped chassis 300. To this chassis 300, the central sheet 260 and the bodily fluid-absorbent structure 1B are attached. The front side leg elastic members $14_F$ included by the front sheet assembly 270 of the developed diaper 1a shown by FIG. 8 is sandwiched between inner sheet 271 and the outer sheet 272 wherein the font side upper ends 74 and the vicinity thereof are spaced from the front side peripheral edges $15_F$ as a part of the peripheral edges 15 of the leg-openings 12 (See FIG. 1). In consequence, regions 270a constituting a part of the front sheet assembly 270 and including none of the front side leg elastic members $14_F$ are defined between the respective lower edges 73 of the front side upper ends 74 and the front side peripheral edges $15_F$. The rear side leg elastic members $14_R$ included by the rear sheet assembly 280 as shown in FIG. 8 are sandwiched between the inner sheet 281 and the outer sheet 282 and cooperate with these inner and outer sheets 281, 282 to form the rear side peripheral edges $15_R$ constituting part of the peripheral edges 15 of the leg-openings 12 (See FIG. 1).

Such developed diaper 1a of FIG. 8 may be folded back along the central line D-D and then the respective opposite side edges 7a; 8a which are the same in a dimension in the front-back direction Y may be subjected to the ultrasonic sealing treatment or the hot embossing treatment to obtain the diaper having substantially the same shape as the diaper 1 of FIG. 1. In the diaper obtained in this manner, each of the put flat and joined together regions 50 (See FIG. 1) includes the segment 280b defined by the lower end of the side edge 8a and containing the rear side leg elastic member $14_R$ and the segment 270a corresponding to the lower end of the side edge 7a. This unique arrangement makes it possible to prevent the side edges 7a; 8a might readily begin at the peripheral edges of the respective leg-openings to be peeled off from each other. The segments 280b are fusion-bonded preferably to at least one of the inner sheet 271 and the outer sheet 272 in the segments 270a and more preferably to both the inner sheet 271 and the outer sheet 272. In the diaper obtained from the developed diaper 1a as shown in FIG. 8 in this manner, depending on the size of the respective segments 270a, these segments 270a may be formed with the frills adapted to be visually recognized from the front side of the diaper as the front side leg elastic members $14_F$ contract in the length direction thereof. On the other hand, contraction of the rear side leg elastic members $14_R$ may cause the inner sheet 281 and the outer sheet 282 to get finely wrinkled but may not cause the inner sheet 281 and the outer sheet 282 to be formed with the frills adapted to be visually recognized from the rear side of the diaper. Referring to FIG. 8, the manner in which the front side leg elastic members $14_F$ extend along the respective front side peripheral edges $15_F$ of the peripheral edges 15 and the manner in which the rear side leg elastic members $14_R$ extend along the rear side peripheral edges $15_R$ of the peripheral edges 15 may be adjusted by appropriately adjusting the operation mode of the rocking arm 561 in the equipment exemplarily illustrated in FIGS. 5 and 6.

Placement mode of the front side leg elastic members $14_F$ and the rear side leg elastic members $14_R$ relative to the diaper 1 is not limited to the exemplarily illustrated placement. For example, it is possible without departing from the scope of the present invention to apply the placement mode of the front side leg elastic members $14_F$ in the illustrated embodiment to the rear side leg elastic members $14_R$ and to apply the placement mode of the rear side leg elastic members $14_R$ in the illustrated embodiment to the front side leg elastic members $14_F$. The present invention having been described on the basis of the pants-type disposable diaper may be applicable also to the other pants-type wearing articles such as disposable pants, disposable pants for incontinent patient and toilet-training pants.

REFERENCE SIGNS LIST 1 wearing article (diaper)
6 crotch region
7 front waist region
7a side edges
8 rear waist region
8a side edges
9a (sealing) spots
12 leg-openings
$14_F$ belt-like leg elastic member
$14_R$ belt-like leg elastic member
15 peripheral edges
$15_F$ peripheral edge (front side peripheral edge)
$15_R$ peripheral edge (rear side peripheral edge)
50 put flat and joined together regions
73 lower edge
74 front side upper end
80 frill
83 lower edge
84 rear side upper end
271 sheet-like member
272 sheet-like member
281 sheet-like member
282 sheet-like member
X transverse direction
Y front-back direction
Z vertical direction

The invention claimed is:

1. A disposable pants-type wearing article having a front-back direction, a vertical direction and a transverse direction being orthogonal to one another, the article comprising:
    a front waist region and a rear waist region opposed to each other in the front-back direction and a crotch region extending between the front and rear waist regions;
    joined regions formed by putting flat and joining together the front and rear waist regions along respective side edges of the front and rear waist regions respectively opposed in the transverse direction and extending in the vertical direction;
    a waist-opening and a pair of leg-openings formed by the front and rear waist regions with the crotch region; and
    belt-shaped leg elastic members extending under tension along respective peripheral edges of the leg-openings;
wherein
    the belt-shaped leg elastic members include at least one of natural rubber and synthetic rubber so as to be provided with stretch property and have a skin-facing side covered with a sheet member formed of at least one of a nonwoven fabric and a plastic film,
    the belt-shaped leg elastic members further include front side upper ends lying in the joined regions at the front waist region and rear side upper ends lying in the joined regions at the rear waist region,
    the front side upper ends include, in the joined regions, a first pair of lower edges of the belt-shape leg elastic members,
    the rear side upper ends include, in the joined regions, a second pair of lower edges of the belt-shape leg elastic members, and the lower edges in the second pair extending in parallel to the lower edges in the first pair,
    the lower edges of the belt-shaped leg elastic members at the front side upper ends and the lower edges of the belt-shaped leg elastic members at the rear side upper ends in the joined regions are displaced from each other in the vertical direction so that one of (i) the first pair and (ii) the second pair of the lower edges lies below the other pair of the lower edges, and
    the one pair of the lower edges that lies below is fusion-bonded to the sheet member covering the other pair of the lower edges at a level lower than the other pair of the lower edges.

2. The wearing article defined by claim 1, wherein
the one pair of the lower edges is contiguous to edges of the crotch region, and
the edges of the crotch region are configured to extend circumferentially around wearer's legs, respectively, and define parts of entire peripheral edges of the leg-openings.

3. The wearing article defined by claim 1, wherein
the one pair of the lower edges is contiguous to edges of the crotch region, and
the edges of the crotch region configured to extend circumferentially about wearer's legs respectively cause, upon contraction of the belt-shaped leg elastic members, the sheet member to be formed along parts of entire peripheral edges of the leg-openings with frills.

4. The wearing article defined by claim 1, wherein the one pair of the lower edges are included in the front side upper ends and the other pair of the lower edges are included in the rear side upper ends.

5. A disposable pants-type wearing article having a front-back direction, a vertical direction and a transverse direction being orthogonal to one another, the article comprising:
 a front waist region and a rear waist region opposed to each other in the front-back direction and a crotch region extending between the front and rear waist regions;
 joined regions formed by putting flat and joining together the front and rear waist regions along respective side edges of the front and rear waist regions respectively opposed in the transverse direction and extending in the vertical direction;
 a waist-opening and a pair of leg-openings formed by the front and rear waist regions with the crotch region; and
 belt-shaped leg elastic members extending under tension along respective peripheral edges of the leg-openings;
wherein
 each of the belt-shaped leg elastic members includes at least one of natural rubber and synthetic rubber so as to be stretchable, and has a skin-facing side covered with a sheet member formed of at least one of a nonwoven fabric and a plastic film, and
for each of the leg openings,
 the belt-shaped leg elastic members include
  a front side leg elastic member having a front side upper end lying in the joined region at the front waist region, and
  a rear side leg elastic member having a rear side upper end lying in the joined region at the rear waist region,
 the front side upper end includes, in the joined region, a first lower edge of the front side leg elastic member,
 the rear side upper end includes, in the joined region, a second lower edge of the rear side leg elastic member,
 the first and second lower edges extend in parallel to each other and are displaced from each other in the vertical direction so that one of the first and second lower edges lies below the other lower edge, and
 the one lower edge that lies below is fusion bonded to the sheet member covering the other lower edge at a level lower than the other lower edge.

\* \* \* \* \*